United States Patent [19]

Putman

[11] Patent Number: 5,597,146
[45] Date of Patent: Jan. 28, 1997

[54] RAIL-MOUNTED STABILIZER FOR SURGICAL INSTRUMENT

[76] Inventor: J. Michael Putman, 3707 Gaston Ave., Suite 410, Dallas, Tex. 75246

[21] Appl. No.: 314,517

[22] Filed: Sep. 28, 1994

Related U.S. Application Data

[63] Continuation-in-part of Ser. No. 15,393, Feb. 8, 1993, Pat. No. 5,351,676, which is a continuation of Ser. No. 740,413, Aug. 5, 1991, Pat. No. 5,184,601.

[51] Int. Cl.$^6$ .................................................. A61B 1/00
[52] U.S. Cl. ...................... 248/276.1; 248/550; 248/662; 248/176.3
[58] Field of Search .................... 248/279, 183, 248/184, 278, 276, 177, 550, 285, 286, 287, 662, 652, 186.2, 178.1, 176.3, 283.1, 285.1, 276.1; 128/4, 17, 20; 606/46

[56] References Cited

U.S. PATENT DOCUMENTS

| | | | |
|---|---|---|---|
| 552,693 | 1/1896 | Myers | 248/279 X |
| 2,944,120 | 7/1960 | Ruben | 200/5 R |
| 3,043,448 | 7/1962 | Melton | 901/17 X |
| 3,221,743 | 12/1965 | Thompson et al. | 248/279 X |
| 3,297,291 | 1/1967 | Everett | 248/283.1 X |
| 3,575,301 | 4/1971 | Panissidi | 901/16 X |
| 3,929,209 | 12/1975 | De Vore | 248/279 X |
| 3,986,692 | 10/1976 | Kinoshita | 248/160 |
| 4,170,336 | 10/1979 | Malis | 248/276 |
| 4,229,136 | 10/1980 | Panissidi | 901/16 X |
| 4,349,014 | 9/1982 | Takamatsu | 128/6 |
| 4,458,870 | 7/1984 | Duncan et al. | 248/279 |
| 4,510,926 | 4/1985 | Inaba | 128/20 |
| 4,572,594 | 2/1986 | Schwartz | 312/209 |
| 4,573,452 | 3/1986 | Greenberg | 128/20 |
| 4,593,681 | 6/1986 | Soni | 128/4 |
| 4,601,284 | 7/1986 | Arakawa et al. | 128/6 |
| 4,607,897 | 8/1986 | Schwartz | 312/209 |
| 4,649,323 | 3/1987 | Pearlman et al. | |
| 4,733,138 | 3/1988 | Pearlman et al. | |
| 4,796,846 | 1/1989 | Meier et al. | 248/287 X |
| 4,854,301 | 8/1989 | Nakajima | 128/4 |
| 4,856,741 | 8/1989 | Schafer | 248/285 X |
| 4,863,133 | 9/1989 | Bonnell | 248/288.3 X |
| 4,865,484 | 9/1989 | McConnell | 248/286 X |
| 4,867,404 | 9/1989 | Harrington et al. | 248/231.4 |
| 4,969,625 | 11/1990 | Singer et al. | 248/662 |
| 4,971,037 | 11/1990 | Pelta | 128/20 |
| 5,061,018 | 10/1991 | Pederson et al. | 312/209 |

FOREIGN PATENT DOCUMENTS

| | | |
|---|---|---|
| 0239409 | 9/1987 | European Pat. Off. . |
| 0326768A3 | 8/1989 | European Pat. Off. . |
| 0456103A3 | 11/1991 | European Pat. Off. . |
| 0456103A2 | 11/1991 | European Pat. Off. . |
| 2390615 | 1/1979 | France ................................. 248/660 |
| 1269827 | 11/1986 | U.S.S.R. . |
| 2212655 | 12/1990 | United Kingdom . |
| 2232655 | 12/1990 | United Kingdom . |

OTHER PUBLICATIONS

Brochure, "Elmed Endoscopic Fixation Device", Elmed Incorporated (not dated).
European Search Report dated 09 Jun. 1993 for EP 92 30 8413 which derives its priority from U.S. Application 07/740,413.

*Primary Examiner*—Ramon O. Ramirez
*Assistant Examiner*—Brian J. Hamilla
*Attorney, Agent, or Firm*—Dennis T. Griggs

[57] ABSTRACT

A rail-mountable support assembly includes a universal positioning arm for holding a surgical instrument such as an endoscope or retractor during a surgical procedure. Coarse adjustment of instrument X-Y position across the sterile field above an operating table is provided by an articulated arm which is rotatably coupled to an upright support shaft. Fine adjustment of surgical instrument elevation above the operating table is provided by a reversible drive motor which extends and retracts the instrument along the longitudinal axis of the support arm. The insertion orientation of the instrument is adjustable by a rotatable coupling. Release of the articulated arm for coarse positioning can be performed manually by actuation of an arm-mounted switch, and fine positioning can be performed manually by arm-mounted switches or by foot pressure applied to floor switches by the surgeon.

9 Claims, 7 Drawing Sheets

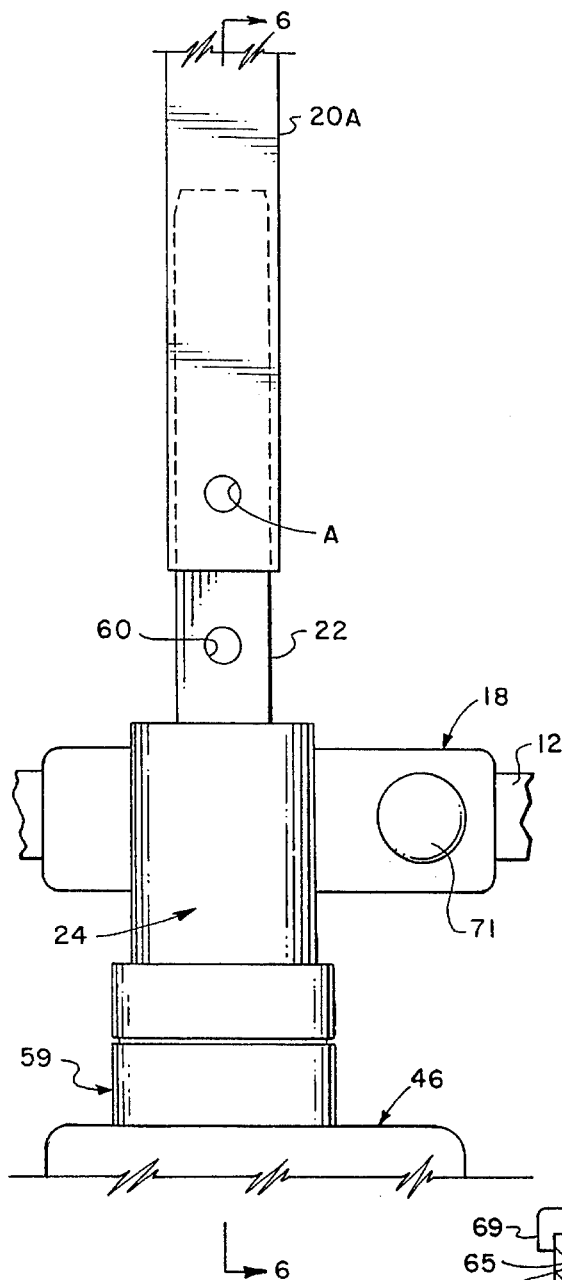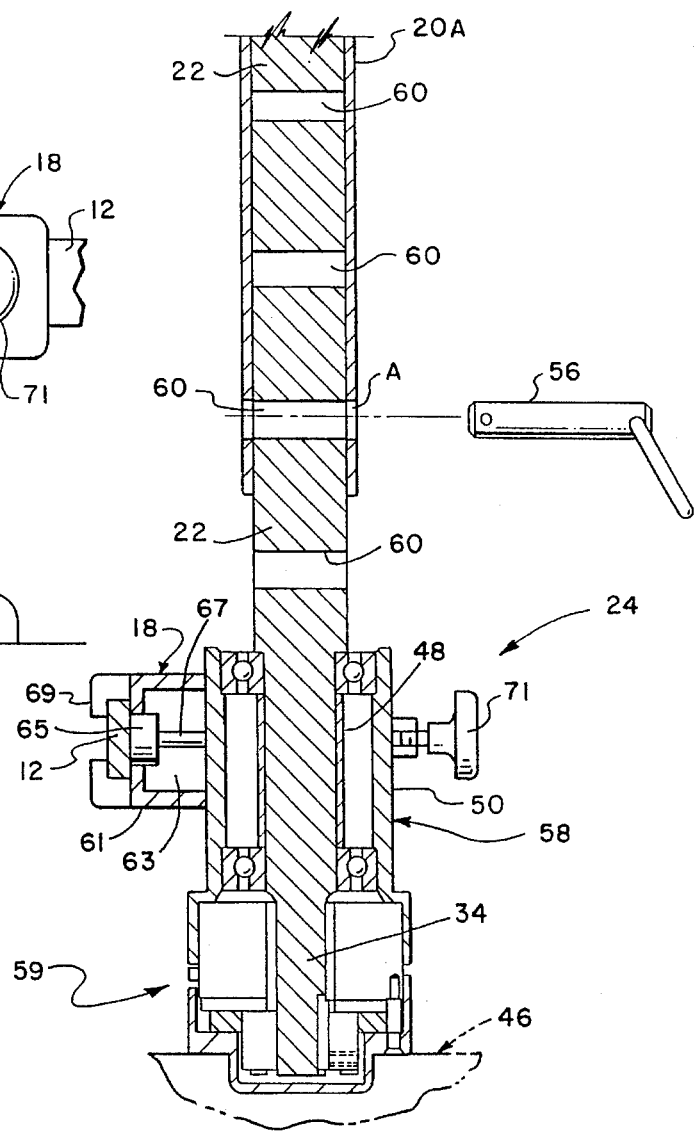
FIG. 5
FIG. 6

RAIL-MOUNTED STABILIZER FOR SURGICAL INSTRUMENT

CROSS-REFERENCE TO RELATED APPLICATIONS

This application is a continuation-in-part of application Ser. No. 08/015,393, filed on Feb. 8, 1993 and issued as U.S. Pat. No. 5,351,676 on Oct. 4, 1994, which is a continuation of application Ser. No. 07/740,413, filed on Aug. 5, 1991 and issued as U.S. Pat. No. 5,184,601 on Feb. 9, 1993.

FIELD OF THE INVENTION

This invention relates generally to the art of universal positioning devices, and in particular to rail-mounted apparatus for selectively positioning and stabilizing an instrument such as an endoscope or retractor during a surgical procedure.

BACKGROUND OF THE INVENTION

In the performance of surgery and related procedures, it is sometimes necessary to support and stabilize a surgical instrument such as endoscope in an elevated position above an operating table for long periods of time, with a portion of the instrument being inserted into the patient's abdominal cavity. An endoscope is a slender viewing tube which may be rigid or flexible, and includes an optical lens system and a light source. The purpose of the endoscope instrument is to provide visual access within a body cavity, for example, the abdominal cavity, the knee, shoulder, bladder, uterus or bowel. A laparoscope is a type of endoscope which includes a rigid viewing tube for insertion through the abdominal wall.

It is necessary to vary the position of the instrument from time-to-time according to the needs of the surgical procedure. During a laparoscopic cholecystectomy (gall bladder removal), for example, an endoscope is inserted in the upper abdominal cavity which is inflated and pressurized with carbon dioxide by an insufflating machine. The endoscope is guided through a trocar sheath which serves as an interface port through the abdominal wall. By sliding the endoscope up and down the port, or rotating in the desired direction, a view of the internal organs can be obtained by a video camera which is attached to the endoscope, with the image being displayed on a video monitor.

The video camera also monitors the movement of other surgical instruments, for example, a grasper, a hook, a spatula, forceps and dissector, which are guided into and out of the abdominal cavity through one or more secondary surgical trocar sheaths. When the distal tip of the instrument appears on the video monitor, the surgeon guides it into place and controls its action and movement as it is displayed on the video monitor. It is usually necessary to re-position the endoscope from time-to-time to view the operative site so that the surgical instruments are positioned appropriately within the cavity to expose the organ or internal tissue for inspection, repair, dissection or excision.

The success of such procedures depends in part on the surgeon's ability to judge spatial relationships as viewed on the video monitor, and to be able to easily adjust or re-position the surgical instrument as the procedure progresses. During gall bladder removal, for example, it may be necessary to re-position the endoscope and hold it in a desired orientation as the gall bladder duct is sealed by a surgical clip. Additionally, it may be necessary to re-position the endoscope while using an electrocautery instrument to excise the gall bladder from the underside of the liver. After the gall bladder organ has been severed, it is removed through an exit port. It is then necessary to re-position the endoscope to an upper midline port so that the surgeon can correctly position and operate a grasper instrument through a secondary trocar port.

Examples of the procedures which may be performed or assisted by endoscopy include the following:

| Diagnostic | Tubal Sterilization | Ablation Endometriosis |
|---|---|---|
| Ovarian Biopsy | Ovarian Cyst Aspiration | Ovarian Cystectomy |
| Ovarian Endocoagulation | Oophorectomy | Laser Uterine Nerve Ablation |
| Presacral Neurectomy | Salpingoplasty | Salpingostomy |
| Salpingectomy | Tubal Reanastomosis | Myomectomy |
| Pelvic Abscess | Removal of foreign body (IUD) | In Vitro Fertilization |
| Hysterectomy | Ovarian Torsion | Multiple Peritoneal Biopsies |
| Omentectomy | Lymphadenectomy | Lysis Bowel Adhesions |
| Appendectomy | Cholecystectomy | Colectomy |
| Hernia Repair | Gonadectomy | Nephrectomy |

Other procedures which may be assisted by endoscopy include orthopedic knee surgery, orthopedic shoulder surgery, urological procedures, bowel procedures, and other gynecological procedures.

DESCRIPTION OF THE PRIOR ART

In the performance of surgical procedures within the abdominal cavity in which an endoscope instrument is utilized, the endoscope instrument is inserted into the abdominal cavity and must be supported and held in a fixed position during the procedure, and its position must be adjusted from time-to-time. Once the precise anatomy-viewing position is established, it must be securely maintained. Otherwise, the physician's view will be interrupted, with loss of visual contact at a critical moment during the operation, which prolongs the procedure. Moreover, the endoscope instrument might, due to slippage, exert pressure on tissues and soft organs such as the liver, pancreas and intestines.

In some cases, operating room personnel manually hold the surgical instrument in the desired position, and move it about according to the surgeon's instructions. The use of operating room personnel to support such instruments during an extended surgical procedure is unsatisfactory in that the assistant may be unable to maintain stability because of muscle fatigue, and find it necessary to change position at some critical or otherwise inconvenient time.

Support devices which are mountable on the side rail of an operating table have been used for holding surgical instruments such as endoscopes and retractors. Such instruments must be moved about from time-to-time as required by the surgical procedure. However, some conventional support devices restrict access to the surgical site and have limited maneuverability.

Operating tables are provided with narrow side rails on which surgical support equipment may be attached. However, because the side rails are located near the sterile operating field, certain instrument support positions are difficult to achieve. Generally, it is desirable to support surgical instruments in offset relation with respect to the operating table and side rails to allow a wide range of support positions across the sterile field.

Moreover, some conventional rail-mounted positioning equipment must be manually released from time-to-time to re-position instruments which are suspended above the sterile field. It will be appreciated that in surgical procedures, time is of the essence and delays associated with adjustment of support equipment prolong the procedure. Additionally, the presence of surgical support equipment within the sterile operating field limits the surgeon's access to the patient during the procedure. Consequently, it is generally desirable to limit the number of surgical support devices in and about the sterile zone so that the operating surgeon and his attendants will have clear and unrestricted access to the patient, and also will have a clear and unrestricted view of patient monitoring equipment.

During certain procedures, it may be desirable to impose or change a biasing force on the surgical instrument to stabilize its position within the surgical cavity. It is desirable to offset such support equipment both laterally and vertically in the regions immediately surrounding the sterile field of the operating table so that the appropriate bias forces may be applied, without restricting the surgeon's access to the patient.

OBJECTS OF THE INVENTION

Accordingly, there is a specific need for surgical instrument support apparatus which may be attached to the side rail of an operating table outside of the sterile field for supporting a surgical instrument, such as an endoscope or retractor, at a desired position and orientation within a body cavity, with the position of the instrument supporting apparatus being stable when set, and being easily and quickly adjustable to other support positions as desired.

One object of the present invention is to provide an improved rail-mountable surgical instrument support apparatus having an articulated arm which can be extended and moved about within the sterile field overlying an operating table, thereby providing stable support for a surgical instrument at an unlimited number of internal positions.

A related object of the present invention is to provide an improved rail-mountable surgical instrument support apparatus as described, in which an articulated support arm may be raised and lowered as desired within the sterile field overlying an operating table, thereby providing a wide range of instrument orientations and patient clearance elevations.

Yet another object of the present invention is to provide a portable, light-weight surgical instrument support assembly having an articulated support arm in which the support assembly can be hand-carried and quickly set up on the side rail of an operating table, with the articulated arm being quickly adjustable to a desired orientation relative to the patient.

Another object of the present invention is to provide a surgical instrument support apparatus having an articulated arm as described, with the position of the articulated arm being subject to coarse control adjustment during initial set up by an attendant, and subject to fine control adjustment by a surgeon during a surgical procedure.

A related object of the present invention is to provide surgical instrument support apparatus of the character described in which the fine control adjustment is performed by the surgeon actuating a foot switch assembly during the course of a surgical procedure.

Still another object of the present invention is to provide a surgical instrument support apparatus of the type described, in which remotely operable means are provided for locking and releasing the joints of the articulated arm so that it can be quickly re-positioned by the surgeon during the course of a surgical procedure.

Yet another object of the present invention is to provide an improved surgical instrument support apparatus of the character described, which is capable of stable attachment to the side rail of an operating table in a configuration which provides both lateral and vertical offset clearance with respect to the sterile zone.

SUMMARY OF THE INVENTION

The present invention provides a rail-mountable support assembly having a universal positioning arm for holding and stabilizing a surgical instrument such as an endoscope or retractor during a surgical procedure, which is quickly and easily adjustable over a wide range of stable support positions.

The support assembly of the present invention includes an articulated positioning arm and means for adjusting the elevation and orientation of a surgical instrument within a sterile field above or about a conventional surgical operating table. In particular, the apparatus of the present invention includes a rail clamp for anchoring the positioning apparatus on the side rail of an operating table and a vertical support shaft is mounted on the rail clamp for adjustable movement in elevation. An articulated arm for holding and stabilizing a surgical instrument, such as an endoscope or retractor, is rotatably coupled to the vertical support shaft. The support assembly includes a releasable brake and a positioning drive motor which are controllable by a foot switch for accurately positioning the distal end of a surgical instrument, such as an endoscope or retractor, within a body cavity of a patient who is undergoing surgery. The articulated arm has two sections which are independently rotatable with respect to each other to provide a wide range of position adjustment of the surgical instrument across the sterile field. The joints of the articulated arm are coupled by band brakes which are lockable and releasable upon application of an electrical control signal from a console switch, or upon application of an electrical control signal from a manual release switch attached to the articulated arm.

The features and advantages of the present invention will be further appreciated by those skilled in the art upon reading the detailed description which follows with reference to the drawings, wherein:

BRIEF DESCRIPTION OF THE DRAWINGS

FIG. 5 is a rear elevational view, partially broken away, of the rail-mounted support apparatus of FIG. 1;

FIG. 6 is a sectional view thereof, taken along the lines 6—6 of FIG. 5;

DETAILED DESCRIPTION OF THE PREFERRED EMBODIMENT

Figure 1:
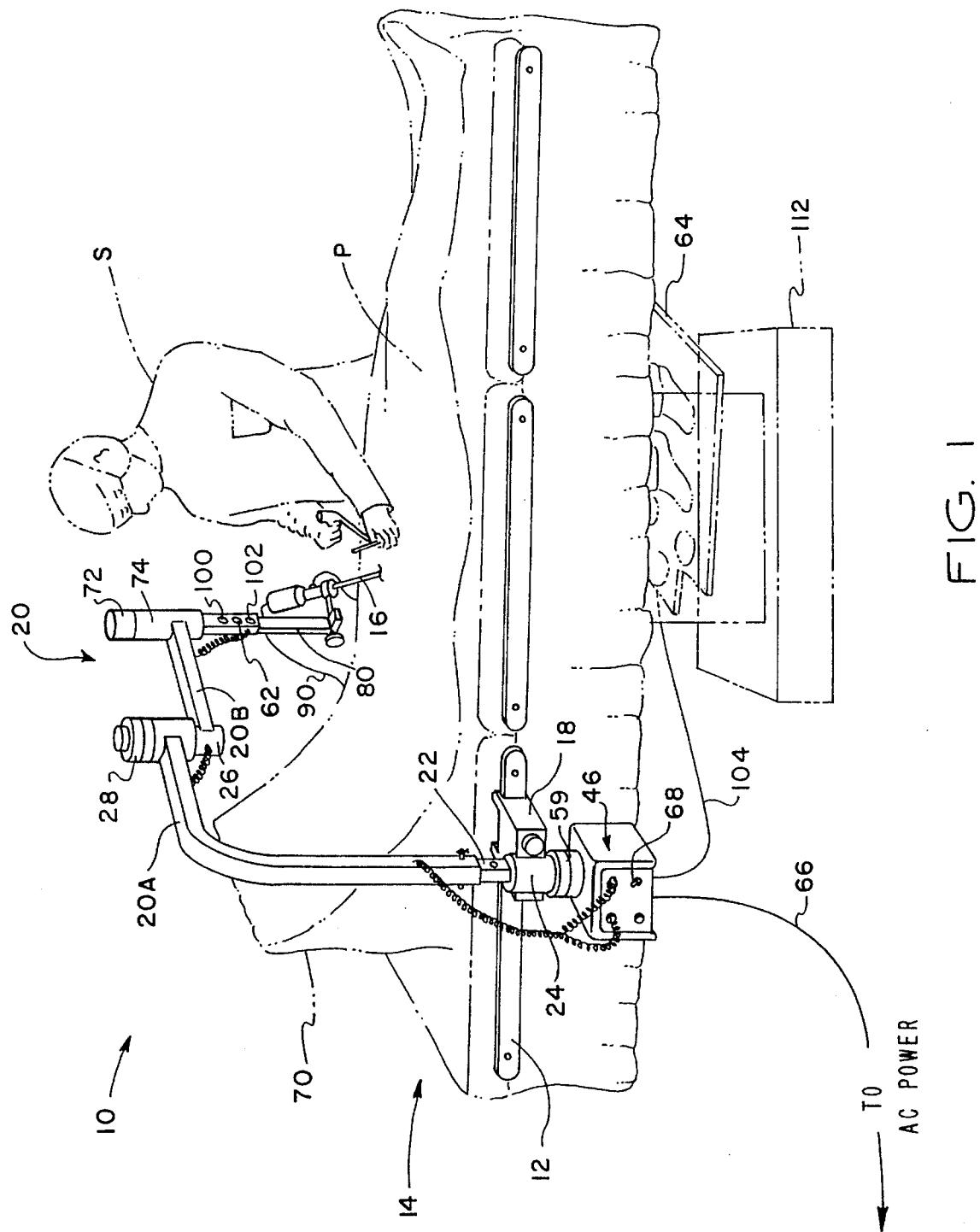
FIG. 1 is a perspective view of the rail-mounted positioning apparatus of the present invention shown attached to the side rail of a surgical operating table.

In the description which follows, like parts are indicated throughout the specification and drawings with the same reference numerals, respectively. The drawings are not necessarily to scale, and the proportions of certain parts have been exaggerated to better illustrate certain structural features.

The surgical instrument support apparatus 10 of the present invention is particularly well suited for use in combination with a conventional surgical operating table 12 during the performance of various surgical procedures, including abdominal, pelvic, joint, bladder, bowel and uterine surgery.

Figure 2:
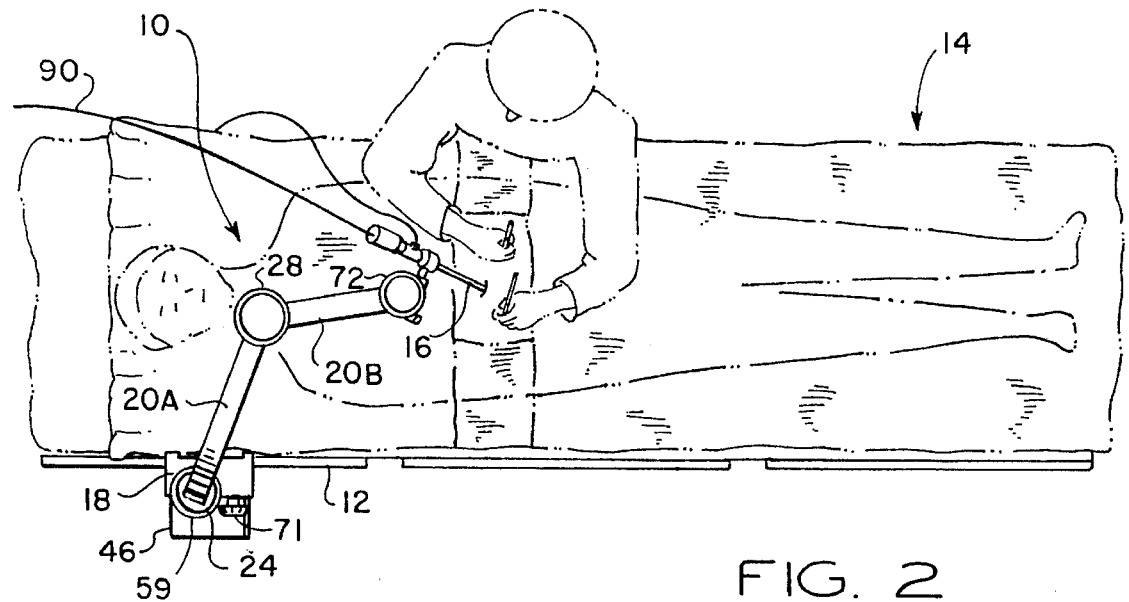
FIG. 2 is a top plan view of the rail-mounted positioning apparatus and surgical operating table as shown in FIG. 1.

Referring now to FIG. 1 and 2, the surgical instrument support apparatus 10 is releasably mounted on the side rail 12 of an operating table 14 for positioning an endoscope 16 during a surgical procedure in the abdominal cavity of a patient P. The support apparatus 10 is anchored to the side rail 12 by a releasable clamp assembly 18, and is located near the head of the operating table to provide standing room for attendants who assist the surgeon S. After the clamp 18 has been locked, the surgical instrument support apparatus 10 is made ready by an attendant.

Figure 3:
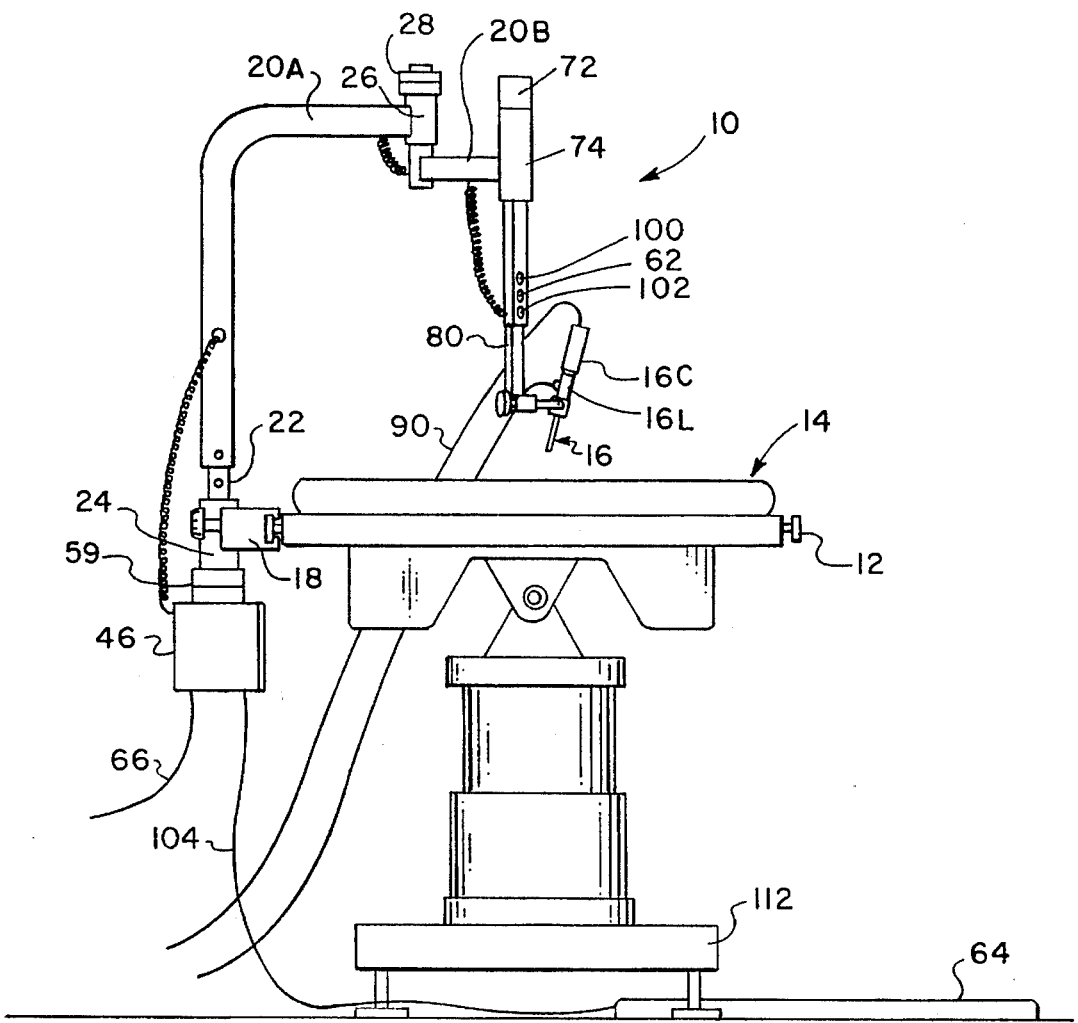
FIG. 3 is a right side elevational view of the positioning apparatus shown in FIG. 1.
Figure 7:
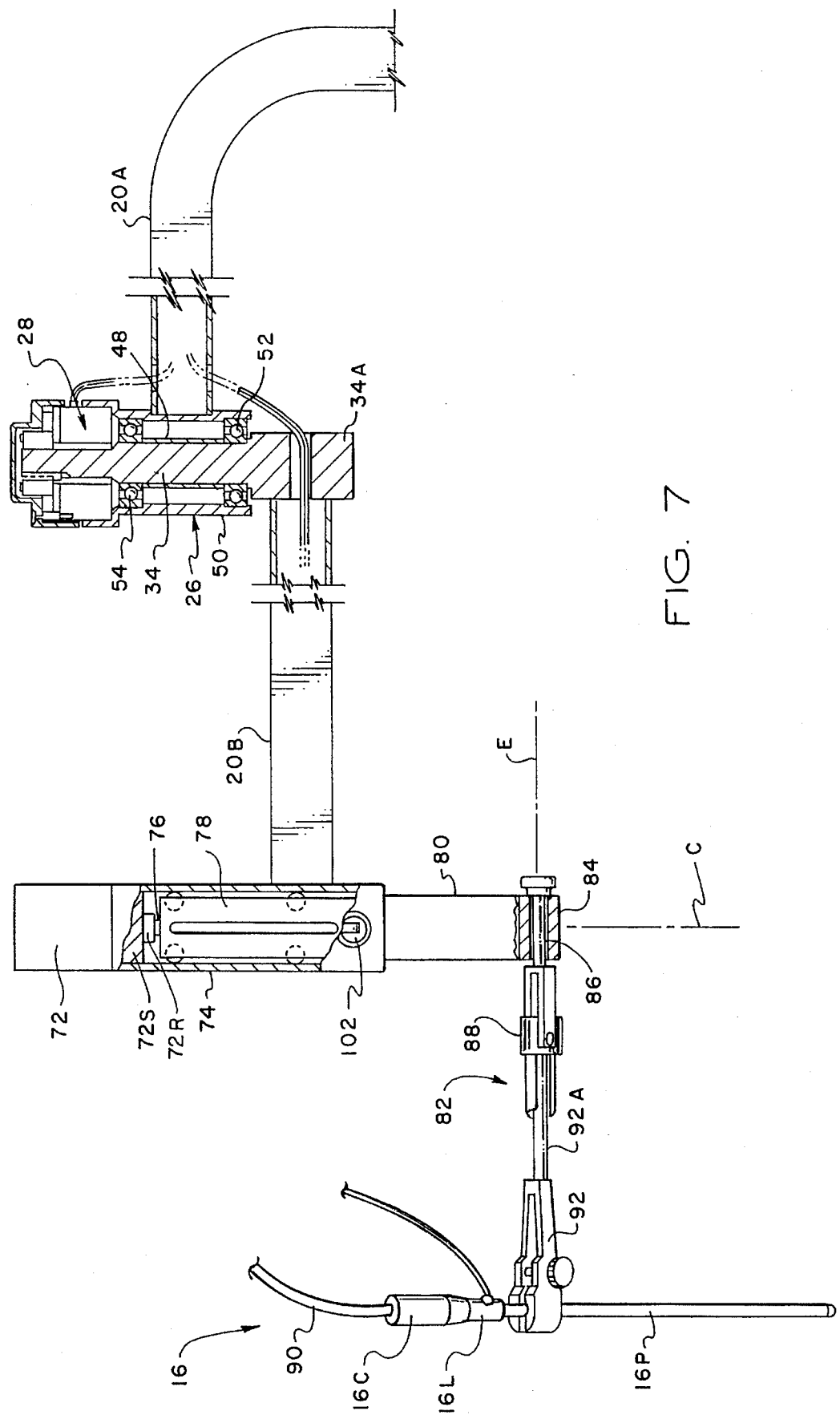
FIG. 7 is a side elevational view, partly in section, of an articulated arm assembly.

The endoscope 16 is supported by an articulated arm assembly 20 which includes a first (proximal) support arm section 20A and a second (distal) support arm section 20B. The articulated arm assembly 20 is supported by an upright support shaft 22. The upright support shaft 22 is rotatably coupled to the rail clamp assembly 18 by a rotary coupling 24 which includes a bearing assembly 58 and a brake assembly 59. (FIG. 6). The first support arm section 20A is slidably coupled in telescoping relation to the upright support shaft 22 which permits adjustment of the elevation of the support arm 20 relative to the upright support shaft 22. Likewise, the second support arm section 20B is rotatably coupled to the first support arm section 20A by a bearing rotary coupling 26 (FIG. 3, FIG. 7). According to this arrangement, the proximal and distal support arm sections 20A, 20B are rotatably coupled together for folding movement relative to each other.

Figure 8:
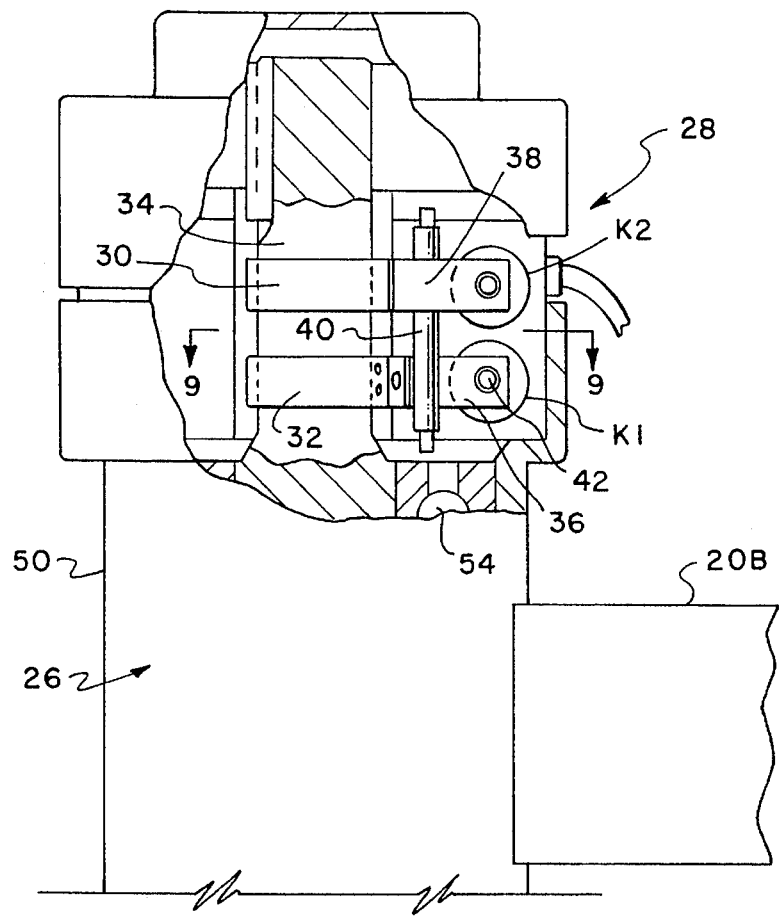
FIG. 8 is an elevational view, partly in section, showing a band brake assembly.
Figure 9:
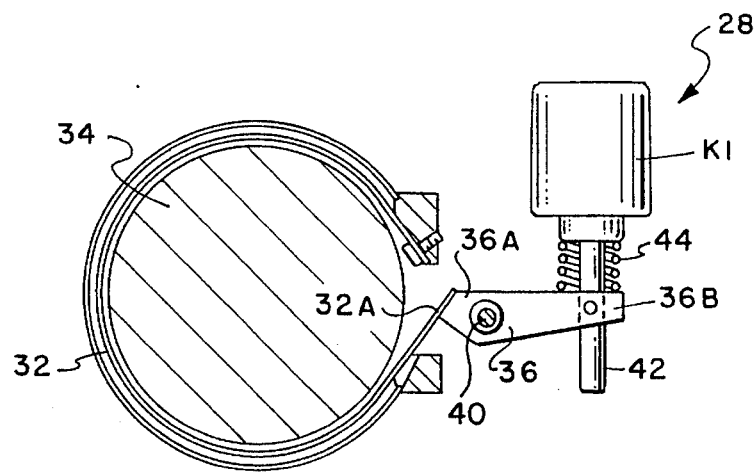
FIG. 9 is a sectional view of a band brake assembly taken along the line 9—9 of FIG. 8; and, FIG. 10 is a simplified control circuit diagram.

The angular position of the first support arm section 20A relative to the second support arm section 20B is selectively locked and released by a band brake assembly 28 as shown in FIG. 7, FIG. 8 and FIG. 9. The band brake assembly 28 includes a pair of friction bands 30, 32 fitted about a coupling shaft 34 and movable from a released, non-engaging position as shown in FIG. 9 to a locked, braked position (FIG. 8) in response to retraction of the friction bands 32, 34. The friction bands 32, 34 are selectively retracted by lever arms 36, 38, each of which are mounted for pivotal movement on a pin 40. One end 36A of the lever arm 36 is connected to the free end 32A of the friction band 32, and the opposite end 36B of the lever arm is attached to the plunger 42 of an electrical solenoid K1. The lever arm 36 is biased to the locked, braked position by a coil spring 44.

According to this arrangement, when the solenoid K1 is energized, the plunger 42 retracts and draws the lever arm end portion 36B in a counterclockwise movement. As this occurs, the bias spring 44 is compressed, thereby releasing the friction band 32 from engagement against the external cylindrical surface of the coupling shaft 34. When operating power is removed from the solenoid K1, the bias spring 44 pushes the lever arm end portion 36B in clockwise movement, thereby drawing the friction bands 32, 34 into engagement with the coupling shaft 34. When power is removed from the solenoids, the second support arm section 20B is locked relative to the first support arm section 20A.

The friction band 30 is operated by a second solenoid K2. The plunger of the second solenoid K2 is connected to the lever arm 38 and is mounted for pivotal movement on the pin 40. The solenoids K1, K2 are electrically coupled in parallel to a source of electrical operating power through a position controller 46 as shown in the electrical circuit diagram of FIG. 10.

The band brake assembly 28 is coupled to the bearing assembly 26 by a sleeve member 48 and is coupled to the first support arm section 20A by a tubular housing 50. The second support arm section 20B is attached to the coupling shaft 34 on the lower end 34A (FIG. 7). Ball bearing members 52, 54 permit rotation of the coupling shaft 34 relative to the housing member 50.

Referring now to FIG. 1, FIG. 3 and FIG. 6, the first support arm section 20A is telescopically coupled to the upright support shaft 22 and is adjustable in elevation relative to the operating table 14 by a latch pin 56. The first support arm section 20A is intersected by a latch aperture A, and the upright support shaft 22 is intersected by multiple bores 60. The latch apertures A are alignable in registration with each bore 60, so that the latch pin 56 may be inserted through the aligned openings for setting the elevation of the first support arm section 20A with respect to the upright support shaft 22. The upright support shaft is integrally formed with the coupling shaft 34. The coupling shaft 34 is rotatably coupled to the rail clamp 18 by the bearing assembly 58.

Figure 4:
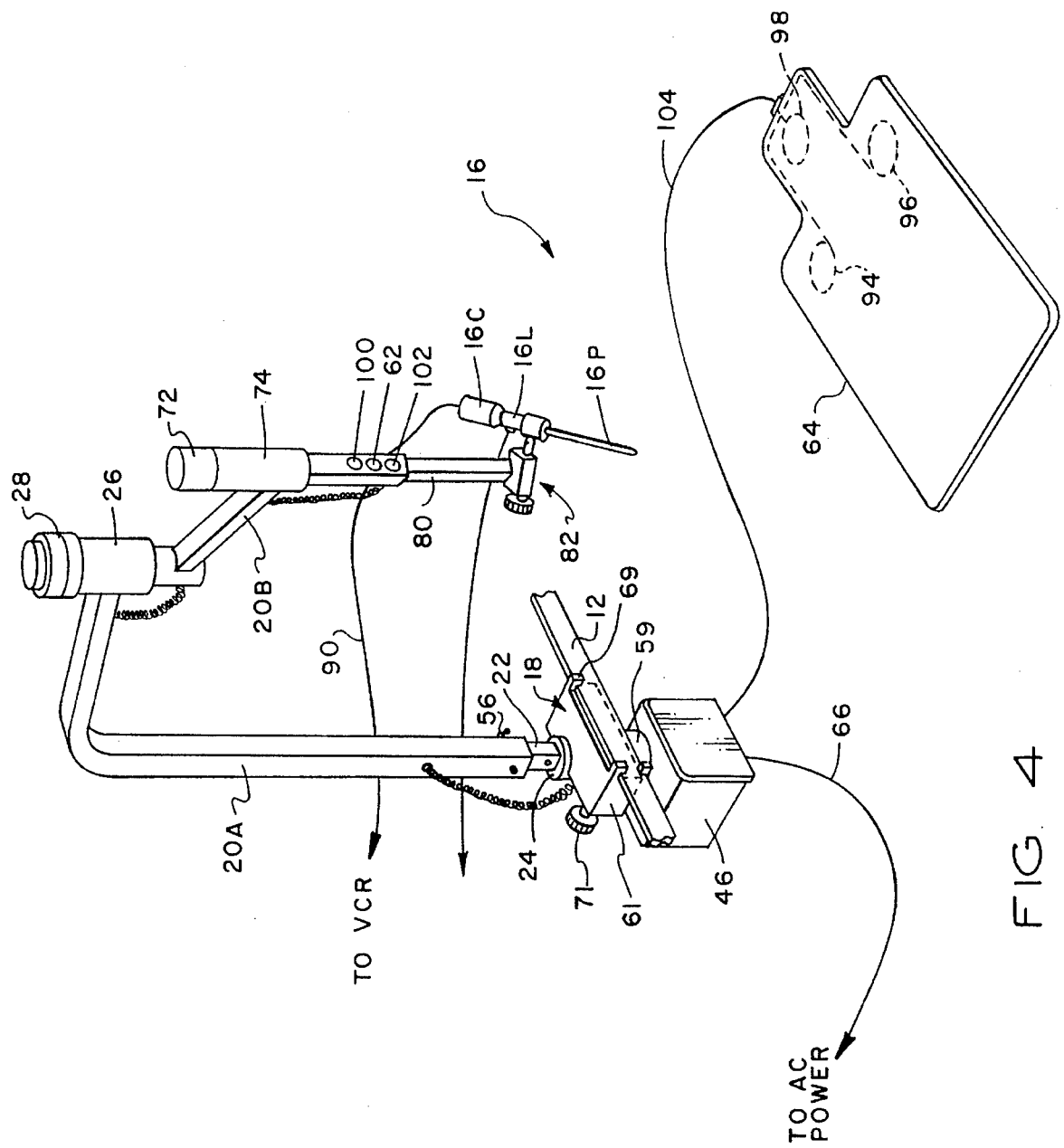
FIG. 4 is a front perspective view of the rail-mounted positioning apparatus of FIG. 1 with the surgical operating table removed.

Referring now to FIG. 4 and FIG. 6, the surgical instrument support apparatus 10 is releasably attached to the side rail 12 by the rail clamp assembly 18. The rail clamp assembly 18 includes a clamp body 61 which is secured to the external housing of the bearing assembly 58. A pocket or cavity 63 is formed within the clamp body 61 for receiving a compression disk 65. The compression disk 65 is coupled to a screw shaft 67. The screw shaft 67 extends through the clamp body cavity for driving the compression disk 65 to an extended position in which the side rail 12 is clamped between a fixed jaw member 69 and the compression disk. By reversing the rotation of the screw shaft 67, the compression disk is movable to a retracted position allowing release and removal of the fixed jaw member and compression member from the side rail 12. The screw shaft 67 is manually operated by a turn knob 71.

Figure 10:
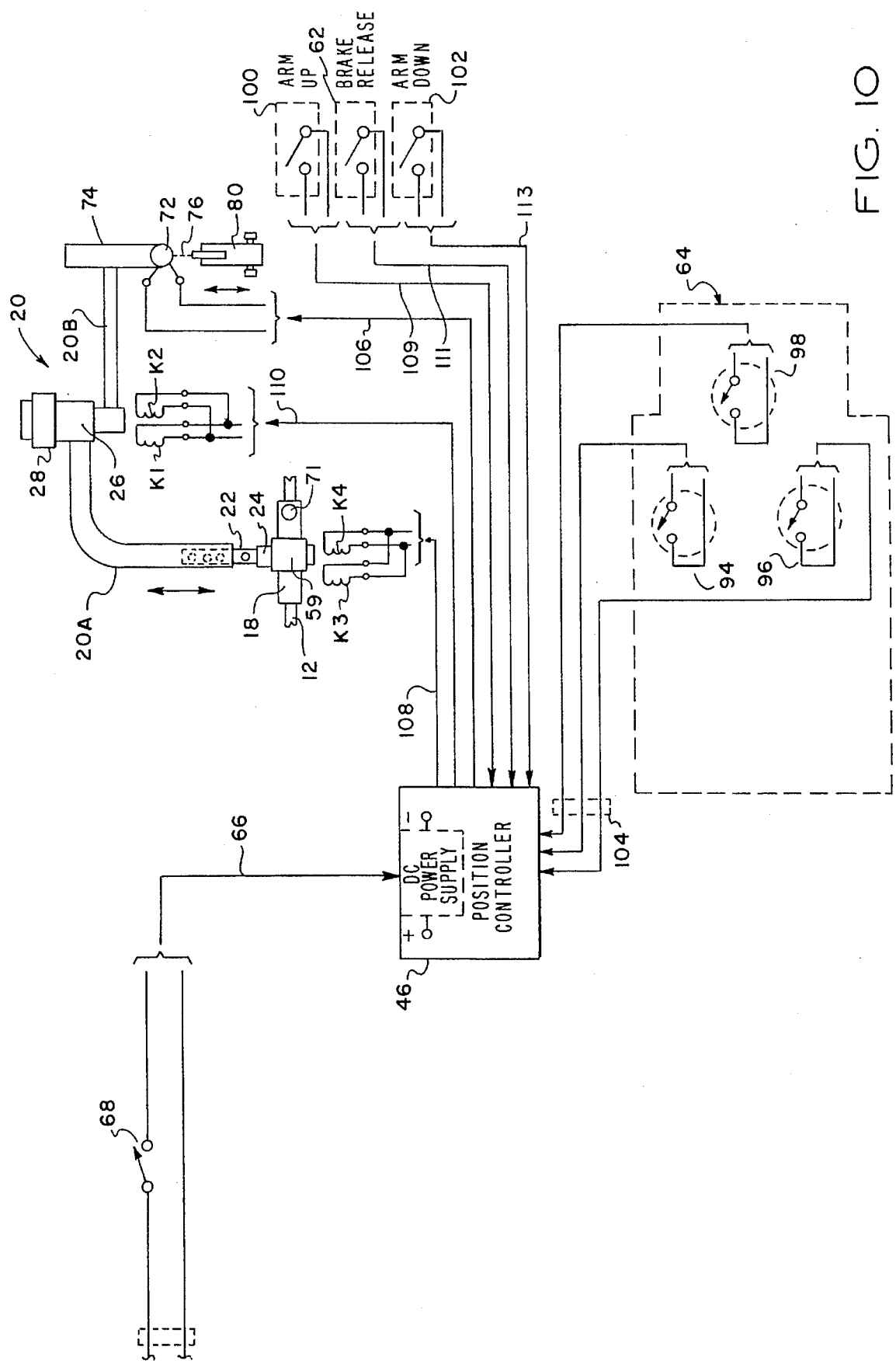

The bearing assembly 58 has substantially the same construction as the bearing assembly 28, with the distal end 34 of the upright support post 22 being releasably engaged by a brake assembly 60. The brake assembly 60 includes a pair of friction bands (not illustrated) which are attached to lever arms and solenoids K3, K4 for selectively locking and releasing the angular position of the upright support shaft 22 with respect to the rail clamp 18. The solenoids K3, K4 are electrically wired in parallel with the solenoids K1, K2 for simultaneously receiving operating power through the position controller 46 as shown in FIG. 10.

Referring again to FIG. 3 and FIG. 10, coarse adjustment of instrument elevation is enabled upon actuation of a brake release switch 62. The brake release switch is a single-pole, non-latching switch which is operable in a momentary ON mode when depressed, and automatically turns OFF when released. Release and lock operation of the solenoids K1, K2, K3 and K4 is enabled by the console-mounted, single-pole, single-throw switch 62. The solenoids are also operable through a floor switch assembly 64 as discussed below.

After the support assembly 10 has been set up and secured to the side rail 12 as shown in FIG. 1, an attendant connects the power service cable 66 to an AC power outlet and makes AC power available to the controller 46 by turning the master switch 68 to the ON position. A DC power supply within the controller 46 provides the DC operating current for the drive motor and solenoids. The elevation of the support arm 20 is manually adjusted until an appropriate clearance elevation has been reached and the desired elevated position is set by the latch pin 56. The solenoids K1, K2, K3 and K4 are then released by depressing the brake control switch 62 and the articulated arm sections 20A, 20B are manually extended over the operating table 14 to place the support arm 20 at an approximate rectangular coordinate X-Y position.

After the approximate X-Y instrument position has been established, the brake control switch 62 is released and the solenoids are de-energized, thereby locking the flexed position of the arms 20A, 20B. A remote video monitor (not shown) is elevated to an appropriate viewing position, and the viewing screen is rotated in alignment with the surgeon's field of view. After the surgical instrument 16 has been attached to the end of the articulated arm, it is covered by a sterile drape 70.

Referring to FIG. 7 and FIG. 10, fine adjustment of instrument elevation above the surgical site along longitudinal axis C is provided by a DC drive motor 72 having a stator member 72S and a rotor member 72R. The stator member 72S of the DC drive motor 72 is mounted within a drive housing 74. A rotor screw shaft 76, attached to the rotor member 72R, is received in threaded engagement with a threaded coupling collar 78 which is extendable and retractable through the drive housing 74. An extendable support arm 80 is attached to the lower end of the coupling collar 78. Upon clockwise and counterclockwise rotation of the rotor screw shaft 76, support arm 80 is extended and retracted along the longitudinal axis C.

Referring again to FIG. 7, the endoscope instrument 16 is secured to the extension arm 80 by a rotatable coupler 82. The coupler 82 is secured for rotation on the distal end of the extension arm 80 by a screw clamp 84. The screw clamp 84 includes a threaded shaft 86 and a coupling collar 88. Upon release of the screw clamp 84 is released, the coupling collar 88 can be rotated about the longitudinal axis E of the threaded shaft 86.

The endoscope instrument 16 is a fiber optic endoscope which has an insertion probe section 16P and a fiber optic video camera 16C. The fiber optic video camera 16C is connected by a signal cable 90 to a remote video recorder unit. A light source 16L is incorporated in the probe section of the endoscope, whereby an image of the internal cavity is provided on a video monitor screen. The probe section 16P of the endoscope is secured by a screw clamp 92. The insertion orientation of the endoscope instrument 16 is adjustable by releasing the screw clamp 84 and rotating the coupling collar 88 until the desired display appears on the viewing screen.

According to this arrangement, the surgeon observes the video presentation and makes fine adjustments of the fiber optic camera orientation by selectively actuating the drive motor 72 after the initial insertion orientation has been established. According to an important feature of the invention, selective actuation of the reversible drive motor 72 is provided by the pressure responsive foot switch assembly 64. The foot switch assembly 64 includes and up and down pressure responsive foot switches 94, 96. A master control release switch 98 is also provided.

The foot switches 94, 96 are non-latching, momentary ON switches which automatically turn OFF in the absence of pressure. The master control release switch 98 is a single-pole, single-throw latching ON switch which is electrically coupled to an enable circuit within the position controller 46. The enable circuit locks up two control switches 100, 102 (arm up, arm down) which are coupled in parallel with the foot switches 94, 96. Actuation of the master control release switch 98 sets the enable circuit, thereby rendering each foot switch active. A second actuation of the master release switch 98 causes the enable circuit to reset, thereby automatically disabling each of the foot switches 94, 96.

If fine adjustment of elevation position is desired during the course of a surgical procedure, the operating surgeon S applies momentary foot pressure to the master release switch 98 which enables the foot switches 94, 96. The surgeon S then applies foot pressure to the appropriate switch until the desired video presentation is obtained. After the desired video presentation is obtained, momentary foot pressure is again applied to the master control switch 98 which disables the fine control switches and prevents inadvertent adjustment.

The foot switches 94, 96 and the master control switch 98 are electrically coupled to the position controller 46 by a multiple conductor cable 104. The position controller 46 applies DC operating voltage of the appropriate polarity to the drive motor 72 in response to actuation of the foot switches 94, 96 or the manual switches 100 (arm up) and 102 (arm down).

The position controller 46 also applies DC operating voltage of the appropriate polarity to solenoids K1, K2, K3 and K4 in response to actuation of the arm mounted brake release switch 62. Preferably, the internal DC power supply within the position controller 46 produces 12 volts DC which is applied in the appropriate polarity to the drive motor 72 through a two-conductor cable 106. The parallel connected solenoids K1, K2, K3 and K4 are likewise simultaneously energized by 12 volts DC through a two-conductor cable 108 and cable 110. The "Arm Up" switch 100, the "Brake Release" switch 62 and the "Arm Down" switch 102 are coupled to the controller 46 by two-conductor cables 109, 111 and 113, respectively.

The fine control drive motor 72 is energized with the appropriate operating voltage polarity by the two-conductor cable 106. The manual brake release switch 62, which is attached to the extension arm 80, is coupled to the position controller 46 by the two-conductor cable 111. This switch and wiring arrangement permits an attendant standing on the other side of the operating table to exercise coarse position control of articulated arm elevation during initial setup. It also permits the surgeon S to exercise coarse and fine position control of the articulated arm assembly, and affords hands free, fine control of instrument elevation by applying foot pressure to selected foot switches.

Referring again to FIG. 1, FIG. 3 and FIG. 6, the surgical instrument support apparatus 10 clamped to the side rail 12 on one side of the operating table, and the foot switch assembly 64 is positioned on the opposite side, adjacent to the operating table support pedestal 112. This orientation of the support apparatus 10 provides access to the surgical site for an attendant, without blocking the surgeon's view of a remote video monitor screen.

The switches 94, 96 and 98, referred to as "pancake" switches, and are sandwiched between two sheets of flexible rubber material. The multiple conductor switch cable 104 is coupled to the position controller 46 by a multiple pin connector which can be plugged in and disconnected from the controller 46 as desired.

Fine positioning control of the endoscope instrument 16 may be accomplished quickly and easily by actuating the appropriate switches on the foot switch assembly 64. The articulated assembly arm 20 can be readjusted as desired by the surgeon by actuating the manual brake release switch 62. Otherwise, the positioning control may be carried out entirely by foot movements, thereby freeing the surgeon's hands for manipulating other surgical instruments, for example, a grasper, hook, spatula, forceps and dissector, as indicated in FIG. 1.

Because the arm assembly 20 is articulated, it can be set up in offset relation to the operating table, out of the sterile field. Because of the stable support provided by the rail-mounted support apparatus 10, no additional support equipment is required. The surgical instrument support apparatus 10 may be set up by one person and requires only minimal training. No additional support personnel are required for holding or stabilizing the endoscope 16. Because of the reach and range of the articulated arm assembly 20, the support assembly can be located on the far end of the operating table, thereby providing access to the surgical site on the near side of the operating table. The sterile drape 70 completely covers the articulated arm assembly and permits the surgeon S to operate freely without contaminating the sterile field. The manual brake release switch 62 is covered by the sterile drape 70 and is actuated by finger pressure applied through the drape.

Referring again to FIG. 7 and FIG. 8, the surgical instrument clamp 92 is sterile and preferably disposable. The clamp 92 is inserted through a preformed opening in the sterile drape 70. The clamp 92 has a shaft portion 92A which is coupled to the collar 88 by a bayonet/detent coupling. The clamp 92 is freely rotatable about the longitudinal axis E. Additionally, the collar 88 is freely rotatable about the longitudinal axis E of the screw clamp 84. The clamp 92 is adjustable, thereby accommodating a wide range of endoscope sizes/diameters.

Upon completion of a surgical procedure, the endoscope 16 is released, articulated arm assembly 20 is retracted, released and folded inwardly, and the rail clamp 18 is released and removed from the table. The surgical instrument support assembly 10 is then ready for storage out of the operating area, and may be hand carried from one operating room to another.

Although the invention has been described with reference to a preferred embodiment, and with reference to a laparoscope instrument, the foregoing description is not intended to be construed in a limiting sense. Various modifications of the disclosed embodiment as well as alternative applications of the invention in other procedures will be suggested to persons skilled in the art by the foregoing specification and illustrations. It is therefore contemplated that the appended claims will cover all such modifications, applications and embodiments as fall within the scope of the invention.

What is claimed is:

1. Surgical instrument support apparatus comprising, in combination:

a rail clamp assembly adapted for releasable attachment to the side rail of an operating table;

an upright support shaft coupled to the rail clamp assembly for rotation relative to the rail clamp assembly;

a support arm assembly coupled to the upright support shaft for holding a surgical instrument during a surgical procedure, the support arm assembly including a proximal support arm and a distal support arm which are movably coupled together for folding movement relative to each other;

first means coupled between the distal support arm and the rail clamp assembly for adjusting the elevation of the distal support arm relative to the rail clamp assembly;

second means coupled between the proximal support arm and the distal support arm for adjusting the angular displacement of the distal support arm with respect to the proximal support arm; and, third means coupled between the rail clamp assembly and the upright support shaft for selectively holding the upright support shaft in a fixed rotational position relative to the rail clamp assembly, and for selectively releasing the upright support shaft so that it can be moved to a different rotational position relative to the rail clamp assembly.

2. Surgical instrument support apparatus as defined in claim 1, said first coupling means comprising:

a telescoping union of the upright support shaft and the proximal support arm, said telescoping union permitting extension and retraction of the proximal support arm relative to the upright support shaft.

3. Surgical instrument support apparatus as defined in claim 1, said second coupling means comprising:

electromechanical control apparatus coupled between the proximal support arm and distal support arm for selectively holding the distal support arm in a fixed angular displacement position relative to the proximal support arm, and for selectively releasing the distal support arm so that it can be moved from the fixed angular position to a different angular position.

4. Surgical instrument support apparatus as defined in claim 1, said third coupling means comprising:

electromechanical control apparatus coupled between the rail clamp assembly and the support shaft for selectively holding the support shaft in a fixed rotational position relative to the rail clamp assembly and for selectively releasing the support shaft so that it can be moved from the first rotational position to a different rotational position relative to the rail clamp assembly.

5. Surgical instrument support apparatus as defined in claim 1, including:

a surgical instrument clamp; and, position adjustment apparatus coupled intermediate the surgical instrument clamp and the distal support arm for extending and retracting the surgical instrument clamp relative to the distal support arm.

6. Surgical instrument support apparatus as defined in claim 5, wherein the position adjustment apparatus comprises:

a reversible drive motor having a housing member mounted on the distal support arm and having a rotor member; and, a torque screw connected to the rotor member and movably coupled to the surgical instrument clamp for extending and retracting the surgical instrument clamp in response to clockwise and counterclockwise rotation of the torque screw, respectively.

7. Surgical instrument support apparatus as defined in claim 1, the rail clamp assembly comprising:

a clamp body coupled to the proximal support arm, the clamp body including a fixed jaw member projecting from the clamp body for engaging the side rail of an operating table, and having a cavity for receiving a compression member;

a compression member mounted within the clamp body cavity for movement to an extended position allowing clamped engagement of an operating table side rail between the fixed jaw portion and the compression member, to a retracted position allowing release of the fixed jaw member and the compression member from the side rail; and, means coupled to the clamp body for driving the compression member from its open, retracted position to its clamped, extended position.

8. Surgical instrument support apparatus as defined by any one of claim 3 or claim 4, including switch control circuit means coupled to the electromechanical control apparatus for enabling and disabling the electromechanical control apparatus.

9. Surgical instrument support apparatus as defined in claim 3 or claim 4, including:

a floor switch control circuit coupled to the electromechanical control apparatus for controlling the extension and retraction of the surgical instrument clamp relative to the distal support arm.

* * * * *